US012752060B2

(12) United States Patent
Jugl et al.

(10) Patent No.: US 12,752,060 B2
(45) Date of Patent: Oct. 6, 2026

(54) WEARABLE ELECTRONIC DEVICE

(71) Applicant: Sanofi, Paris (FR)

(72) Inventors: Michael Jugl, Frankfurt am Main (DE); Stefan Blancke, Frankfurt am Main (DE)

(73) Assignee: SANOFI, Paris (FR)

( * ) Notice: Subject to any disclaimer, the term of this patent is extended or adjusted under 35 U.S.C. 154(b) by 775 days.

(21) Appl. No.: 18/008,517

(22) PCT Filed: Jun. 18, 2021

(86) PCT No.: PCT/EP2021/066533
§ 371 (c)(1),
(2) Date: Dec. 6, 2022

(87) PCT Pub. No.: WO2021/255216
PCT Pub. Date: Dec. 23, 2021

(65) Prior Publication Data

US 2023/0338666 A1 Oct. 26, 2023

(30) Foreign Application Priority Data

Jun. 19, 2020 (EP) .................................... 20315307

(51) Int. Cl.
*A61M 5/315* (2006.01)

(52) U.S. Cl.
CPC . *A61M 5/31568* (2013.01); *A61M 2205/3375* (2013.01)

(58) Field of Classification Search
CPC ...... A61M 5/31568; A61M 2205/3375; A61M 2205/50; A61M 2205/582; A61M 2205/581; A61M 5/3157; A61M 5/31525; A61M 5/31533
See application file for complete search history.

(56) References Cited

U.S. PATENT DOCUMENTS

| | | | |
|---|---|---|---|
| 5,593,390 | A | 1/1997 | Castellano et al. |
| 9,789,260 | B1 | 10/2017 | Binier |
| 10,661,010 | B1 | 5/2020 | Tsinberg |

(Continued)

FOREIGN PATENT DOCUMENTS

| | | |
|---|---|---|
| CN | 101405044 A | 4/2009 |
| CN | 101808684 A | 8/2010 |

(Continued)

OTHER PUBLICATIONS

International Preliminary Report on Patentability in International Appln. No. PCT/EP2021/066533, mailed on Dec. 29, 2022, 8 pages.

(Continued)

*Primary Examiner* — Jason E Flick
(74) *Attorney, Agent, or Firm* — Bond, Schoeneck & King, PLLC

(57) ABSTRACT

The present disclosure relates to a wearable electronic device. The wearable electronic device includes a housing, a processor arranged inside the housing, and at least a first sensor that is connected to the processor and configured to detect at least one of a mechanical vibration or an acoustic noise caused or generated by a click noise generator of a handheld injection device.

20 Claims, 4 Drawing Sheets

(56) References Cited

U.S. PATENT DOCUMENTS

| | | | | |
|---|---|---|---|---|
| 11,311,232 | B2 * | 4/2022 | Arrington | A61M 21/02 |
| 2016/0213853 | A1 * | 7/2016 | Despa | A61M 5/31548 |
| 2017/0172522 | A1 | 6/2017 | Insler et al. | |

FOREIGN PATENT DOCUMENTS

| | | |
|---|---|---|
| KR | 10-2017-0107064 | 9/2017 |
| WO | WO 2004/078239 | 9/2004 |
| WO | WO 2004/078240 | 9/2004 |
| WO | WO 2004/078241 | 9/2004 |
| WO | WO 2016/118736 | 7/2016 |
| WO | WO 2021/255216 | 12/2021 |

OTHER PUBLICATIONS

International Search Report and Written Opinion in International Appln. No. PCT/EP2021/066533, mailed on Jul. 16, 2021, 9 pages.
Notice of Allowance for Chinese Patent Application No. 202180042798.4 issued Jul. 1, 2026 (4 pages, 3 in English).
Search Report for Chinese Patent Application No. 202180042798.4 dated Jun. 25, 2026 (2 pages in English).

* cited by examiner

WEARABLE ELECTRONIC DEVICE

CROSS REFERENCE TO RELATED APPLICATIONS

The present application is the national stage entry of International Patent Application No. PCT/EP2021/066533, filed on Jun. 18, 2021, and claims priority to Application No. EP 20315307.7, filed on Jun. 19, 2020, the disclosures of which are incorporated herein by reference.

TECHNICAL FIELD

The present disclosure relates to a wearable electronic device, in particular to a smart watch configured to be worn by a user of a handheld injection device. In another aspect the disclosure relates to a method of determining a size of a dose or of an operational status of a handheld injection device. A still another aspect the disclosure relates to computer program for determining or detecting a size of a dose, e.g. set or dispensed by a handheld injection device and/or for detecting or determining an operational status of the handheld injection device.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, such as pen-type injectors, have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

For mechanically implemented drug delivery devices but also for electronically implemented drug delivery devices, e.g. injection device equipped with an electric drive, it is desirable to enable a precise, reliable and quasi-automated supervision and/or collection of drug delivery-related data during use of the injection device. Mechanically operated drug delivery and/or injection devices may be equipped with an electronically implemented electronic module serving as an add-on device or data collection device and being configured to monitor user-induced operation of the injection device. Such electronic modules should be rather compact with regards to their geometric size. Generally, such electronic modules can be used as a memory aid and for accurate dose history locking.

Drug delivery devices, such as handheld injection devices typically provide acoustic or haptic feedback during at least one of setting of a dose, dispensing of a dose or completion of a dose dispensing procedure. A user of the device, e.g. the patient is hence provided with an acoustically or haptically detectable feedback signal when the drug delivery device or injection device is in operation. With mechanically implemented handheld injection devices, such as mechanically implemented pen type injectors there is typically provided a kind of a click noise generator providing a characteristic and hence distinguishable click noise during at least one of setting of a dose, dispensing of a dose or when a dose dispensing procedure has been completed.

For a reliable monitoring of long-term or short-term therapy to be conducted with such handheld injection devices it is desirable to provide an automated or semiautomated logging or supervision of repeated uses of such injection devices. There have been reported numerous add-on or auxiliary devices that provide monitoring of the operation and use of handheld injection devices, such as pen-type injectors. Such add-on or auxiliary devices suitable for monitoring or recording operation of handheld injection devices have to be connected mechanically to the respective injection device, e.g. in a predefined way. For disposable injection devices that are intended to be discarded after the medicament provided therein has been used up, the add-on device or auxiliary device has to be detached from the disposable injection device and has to be re-attached to another injection device.

Such repeated disassembly and assembly of an add-on or auxiliary device for the purpose of monitoring operation of a mechanically implemented injection device may provide a burden to the user or patient.

In addition, an assembly comprising a handheld injection device and an add-on or auxiliary device attached thereto features comparatively large geometric dimensions compared to the handheld injection device itself. A handheld injection device equipped with an add-on device or auxiliary device requires an increased storage space, which may be regarded disadvantages when the injection device is carried along by the user or patient.

It is hence desirable to provide an improved system and method to monitor operation or to detect the operational status of a handheld injection device by avoiding the above described disadvantages. The solution should be rather cost efficient and should provide a high level of acceptance by end-users and patients. It is a particular aim to make use of existing hardware components to provide an efficient, precise and reliable monitoring of at least one of a dose setting, a dose dispensing or of an operational status of a handheld injection device.

SUMMARY

In one aspect there is provided a wearable electronic device. The wearable electronic device comprises a housing and a processor arranged inside the housing. The wearable electronic device further comprises at least a first sensor. The first sensor is connected to the processor. The first sensor is configured to detect at least one of a mechanical vibration or an acoustic noise which is caused or generated by a click noise generator of a handheld injection device.

The wearable electronic device is typically worn by the patient or user when using the handheld injection device. The handheld injection device equipped with the click noise generator is typically held in a hand of the user or patient when it is operated by the respective user or patient. Operation of the handheld injection device is accompanied by a respective repeated or regular activation of the click noise generator. A typical use or operation of the handheld injection device is accompanied by at least one, typically by a sequence of distinguishable and/or detectable mechanical vibrations or acoustic noises generated by the click noise generator during operation or handling of the handheld injection device.

The at least first sensor of the wearable electronic device is particularly configured to detect mechanical vibration or acoustic noise that is generated by the click noise generator during use or operation of the handheld injection device. In this way, the processor connected to the at least first sensor and configured to process electrical signals generated and provided by the at least first sensor is enabled to record or to monitor repeated occurrences of mechanical vibration or acoustic signals caused or generated by the click noise generator of the handheld injection device.

With some examples, the processor is configured to count the number of mechanical vibrations or acoustic noises of a sequence of mechanical vibrations or acoustic noises originating from the click noise generator during operation of the handheld injection device. By simply counting numerous instances of e.g. a repeating click noise, the size of a dose set or a size of a dose actually dispensed can be calculated. Typically, during the setting of a dose at each time the size of the dose is increased by a predefined increment the click noise generator generates a mechanical vibration or an acoustic noise that is detectable by the at least first sensor.

Similarly, and during dispensing of a dose, the click noise generator may repeatedly generate a characteristic vibration or a characteristic acoustic noise indicative of an increment of a dose actually dispensed or expelled by the handheld injection device. With some examples, the click noise generator may be only or particularly active e.g. at the end of a dose injection procedure, thus indicating haptically or acoustically, that the process of expelling of a dose has been completed.

With some examples, the handheld injection device is equipped with at least two click noise generators. Here, a first click noise generator generates a first mechanical vibration or a first acoustic noise. A second signal generator generates a second mechanical vibration or a second acoustic noise. Moreover, the first mechanical vibration or the first acoustic noise may be distinguishable from the second mechanical vibration or the second acoustic noise. The first sensor and/or the processor may be further configured to distinguish between a first mechanical vibration and a second mechanical vibration and/or may be configured to distinguish between a first acoustic noise and a second acoustic noise. In this way, and when for instance the first click noise generator is exclusively active during setting of a dose and the second click noise generator is exclusively active during dispensing of a dose the at least first sensor and/or the processor are enabled to distinguish between setting of a dose and dispensing of a dose when detecting or recording a first or second mechanical vibration or acoustic noise generated by a first or second click noise generator, respectively.

In typical scenarios of use, the click noise generator of the handheld injection device and the at least first sensor of the wearable electronic device are mechanically linked by a carrier medium that provides transmission of mechanical vibration or acoustic noise from the click noise generator towards the at least first sensor. A carrier medium may comprise at least one of the at least one or mechanical components of the handheld injection device and the housing of the wearable electronic device as well as biological tissue, such a bone structure or skin of a human body.

Typically, and when operated the handheld injection device is held in a hand of a user. The wearable electronic devices is typically carried or worn at the same hand of the user also carrying or holding the injection device. Insofar, an acoustic noise or acoustic signal as well as mechanical vibration caused or generated by the click noise generator of the handheld injection device may lead to the generation and/or transmission of acoustic waves or mechanical vibrations through a housing of the handheld injection device into and through biological tissue of a hand or arm of a respective user being in mechanical contact with the handheld injection device.

With some examples, the wearable electronic device is carried or worn by a hand or arm of a user that is not the one holding the handheld injection device but which is that particular hand by way of which the user operates the handheld injection device. By way of example, the user may hold the injection device in a left hand and may use the right hand to operate the device, e.g. to set or to dispense a dose. Here, the wearable electronic device may be either worn by the left hand or right hand of the user. With both options, mechanical vibration and/or acoustic noise originating from the click noise generator of the handheld injection device will be mechanically transferred to the right hand and/or to the left hand of a user.

Insofar, the skin or biological tissue of a portion of a body of a patient may serve as a carrier medium for transferring of acoustic noise or mechanical vibration generated by a click noise generator of a handheld injection device during use of the same. The wearable electronic device and the at least first sensor may be particularly configured to detect such acoustic noise or mechanical vibration transmitted via the biological tissue of the patient or user of the handheld injection device.

Insofar, environmental background noise in the surrounding of the wearable electronic device and/or in the surrounding or vicinity of the handheld injection device may be easily faded away or may be blocked. The at least first sensor of the wearable electronic device may be particularly configured to exclusively detect mechanical vibration or acoustic noise generated by the click noise generator of the handheld injection device. Mechanical vibration or acoustic noise originating from the click noise generator may reach the first sensor only via biological tissue of e.g. a hand or arm of the user.

Generally, each body region of a person or user generally suitable for transmission of acoustic noise or mechanical vibrations, e.g. the skin and/or a bone structure is suitable for wearing of the electronic device. With typical examples, the wearable electronic device is configured to be worn at a wrist or at an arm of the user. It is typically to be worn on the same arm or hand of a user which is also holding the injection device prior to or during use of the injection procedure.

Typically, and according to a further example the wearable electronic devices is implemented as a smart watch or as a fitness tracker configured to be carried or worn at a wrist of an arm or hand of a user. Presuming that the handheld injection device is carried or held in the same hand or arm of the user, the wearable electronic device is inherently in close vicinity to the handheld injection device when injection device is actually operated or used by the user.

Moreover, wearable electronic devices, such as smart watches or fitness trackers are nowadays widely used by end-consumers or patients. They provide interconnectivity with further electronic devices, such as smart phones or tablet computers by way of which the data being indicative of a time, date and/or size of a dose actually injected and being collected or stored by the wearable electronic device can be easily transmitted to a healthcare provider for evaluation or supervision purpose.

Usage of at least a first sensor configured to detect at least one of a mechanical vibration or an acoustic noise caused or generated by the click noise generator of a handheld injection device and implementing such a sensor in a smart watch provides a rather elegant alternative to monitor and log the operation, in particular the dose setting or dose dispensing of a handheld injection device. Use of a particular add-on device or auxiliary device, that requires a dedicated mechanical connection or pairing with the handheld injection device may be replaced by the above-described wearable electronic device provided that the wearable electronic device is equipped with a suitable sensor operable to detect at least one of a mechanical vibration or acoustic noise caused or generated by the click noise generator of the handheld injection device.

According to a further example the wearable electronic device comprises a wristband connected to the housing and configured to attach the housing to a portion of a body of a person. The wristband may be implemented as a bracelet. The wristband may be fixedly attached to the housing. The wristband may be flexible and may provide a strap by way of which the wristband can be wrapped around a dedicated portion of the body of the person. Typically, the wristband provides fixing of the housing and hence fixing of the entire wearable electronic device to a wrist, to a hand and/or to an arm of the user also being mechanically coupled to the handheld injection device.

The wristband is particularly suitable for attaching the wearable electronic device to that particular wrist or hand of the user that is holding the handheld injection device at least during setting of a dose or during dispensing of a dose. In this way, and by attaching the wearable electronic device in close vicinity to a hand of the user actually carrying or holding the handheld injection device the wearable electronic device is inherently provides in close vicinity to the handheld injection device. The close vicinity between the wearable electronic device and the handheld injection device is of particular benefit to provide mechanical vibration or acoustic noise with a sufficient signal strength or intensity in the region of the sensor.

When the at least first sensor is configured to detect a mechanical vibration or an acoustic noise transmitted by biological tissue of the user as a carrier medium, a comparatively short distance between the at least first sensor and the click noise generator and hence a comparatively short distance between the wearable electronic device and the handheld injection device is of particular benefit to provide reliable and highly precise measurement results with the at least first sensor.

According to a further example the at least first sensor is one of a mechanical vibration sensor, an acoustic sensor, an ultrasound sensor, an electric capacity sensor and an optical sensor. With all these types of sensors, at least a mechanical vibration or an acoustic noise transmitted through a portion of biological tissue of the person actually holding the handheld injection device while the click noise generator is repeatedly active can be detected with the at least first sensor.

When implemented as an acoustic sensor, the at least first sensor is typically implemented as a directional microphone, e.g. directed onto a portion of the skin of the user when the wearable electronic device is e.g. worn at a particular portion of the body of the person. Mechanical vibration or an acoustic noise originating from the click noise generator during use of the handheld injection device and being transmitted through the biological tissue of the person when holding the handheld injection device can be thus detected or even quantitatively measured by the at least first sensor.

Each click noise generated by the click noise generator typically generates a mechanical vibration that might be transferred from the click noise generator to the housing of the handheld injection device. Furthermore, such a mechanical vibration is inevitably transferred from the housing to the biological tissue, e.g. to the skin of the person actually holding the handheld injection device. Accordingly, the mechanical vibration transferred into or onto the skin or biological tissue of the person will be transmitted via the respective biological tissue until it arrives at the location of the at least first sensor when the wearable electronic device is actually worn by the user.

Activation or use of the click noise generator of the handheld injection device may cause a detectable mechanical vibration of e.g. the skin of the user. An acoustic noise, hence a click sound may be likewise transferred into and transmitted through biological tissue of the person. A vibrational or acoustic stimulation of the carrier medium, e.g. of biological tissue or of the skin of the user is typically detectable by the at least first sensor, in particular when the at least first sensor is implemented as a mechanical vibration sensor or as an acoustic sensor.

The mechanical or acoustic excitation of the biological tissue of the user may be also detectable in the ultrasound spectral range. In this way and when implemented as an ultrasound sensor, the at least first sensor may be equally capable to detect an ultrasound signal that has been caused or generated by the click noise generator during use of the handheld injection device and which has been transferred into and transmitted through the biological tissue of the user to which the wearable electronic device is attached to In a similar way, the at least first sensor may be implemented as an electric capacity sensor. An acoustic or mechanical excitation of e.g. the skin of the person may be also electrically detectable, by an electrostatic capacitive sensing arrangement, e.g. by the electric capacity sensor that may be in direct contact with a portion of the skin.

Moreover, mechanical vibrations or an acoustic stimulation of a skin portion of a user may be also detectable optically. Here, a light source and a light detector, e.g. both provided by the wearable electronic device may be configured to emit electromagnetic radiation and to transmit the electromagnetic radiation onto a portion of the skin of the user. The optical sensor, hence the optical detector may be configured to record or to detect at least a portion of the electromagnetic radiation reflected by the skin. If the skin is subject to a mechanical vibration caused by the click noise generator of the handheld injection device, such a vibration leads to a measurable modification of the direction and/or of the intensity of light reflected by a particular skin portion.

According to a further example the housing of the wearable electronic device comprises a skin contact face. The skin contact face is configured to get in mechanical contact with a portion of a skin of a person wearing the electronic device. The at least first sensor is embedded in the skin contact face or the at least first sensor is arranged on the skin contact face. Typically, the skin contact face is provided on an outside surface of a bottom of the housing. The housing of the wearable electronic device typically comprises a top or top face located opposite to the bottom. On the top, the wearable electronic device typically comprises a display to visually indicate various information to the user of the wearable electronic device, such as time, date or other health related or physiological data, such as heartbeat rate and the like.

By arranging or embedding the at least first sensor in or on the skin contact face, the at least first sensor is inherently directed onto the skin or may even get in direct contact with the skin when the wearable electronic device is suitably worn by the patient or user. By having the first sensor embedded or arranged on or in the skin contact face, an immediate skin contact may be provided for the first sensor as soon as the wearable electronic device is worn by the user or patient.

According to a further example, the at least first sensor protrudes from the skin contact face. Typically, the at least first sensor is located at a predefined distance from the outer edges of the skin contact face, hence at a particular distance from a side edge or all side edges of the bottom of the housing. The at least first sensor may protrude from the skin contact surface in a direction pointing substantially parallel to a surface normal of the skin contact face of the housing. In this way and when the wearable electronic device is suitably attached to the skin portion of the user, it is somehow guaranteed that the at least first sensor gets in direct contact with the skin of the user.

In this way, detrimental effects that may arise from an uneven or rough portion of the skin that may otherwise lead to a somewhat loose contact between the skin and the at least first sensor can be effectively compensated. By having the at least first sensor at least slightly protruding outwardly from the outer surface of the bottom and hence by having the at least first sensor protruding from the skin contact surface a comprehensive and reliable direct contact between the at least first sensor and the respective portion of the skin can be effectively provided.

According to a further example the housing comprises a recess in the skin contact face. The recess comprises a particular depth. It may extend parallel to a direction of the surface normal of the skin contact face. Typically, the recess is also provided offset from the lateral edges or outside edges of the bottom of the housing. Moreover, the at least first sensor is arranged in the recess. The at least first sensor is typically arranged in a bottom of the recess. In this way, the at least first sensor does not protrude outwardly from the skin contact face. Rather, the at least first sensor is arranged inside the recess. In this way, the at least first sensor is effectively protected from getting in direct contact with a portion of the skin when the wearable electronic device is attached to a respective skin portion.

Such a configuration may be of particular benefit when a direct contact between the at least first sensor and the skin should be avoided. This may be the case for examples, wherein the at least first sensor comprises a combination of a light source and a light detector. With a recessed arrangement of the at least first sensor with regard to the skin contact face, a direct contact between the at least first sensor and a skin portion of a user can be effectively avoided. This may be also of particular benefit to enable an alternative way of detecting e.g. a vibration of the skin portion due to operation of the click noise generator of the handheld injection device. For a vibration measurement of the skin a gap between the at least first sensor and a respective portion of the skin may be beneficial.

According to another example the at least first sensor comprises a direction of a maximum sensitivity. The direction of maximum sensitivity is oriented substantially parallel to a surface normal of the skin contact face. In this way can it is somewhat ensured, that the at least first sensor has its highest sensitivity towards a skin of a person when the wearable electronic device is suitably worn by the person and when the skin contact face of the housing of the wearable electronic device is in direct contact with a respective portion of the skin. In this way environmental influences, such as background noise or vibration of the skin caused by other environmental or ambient influences can be disregarded or set aside. When the at least first sensor is implemented as an acoustic sensor, it may comprise a directional microphone, wherein the maximum sensitivity of the directional microphone is typically oriented parallel to a surface normal of the skin contact face.

Generally, the direction of the maximum sensitivity of a directionally measuring first sensor may also slightly deviate from the direction of a surface normal of the skin contact face. With typical examples, the angular offset between the direction of maximum sensitivity of the at least first sensor and the surface normal of the skin contact face should be less than 45°, less than 30°, less than 20°, less than 15° or less and 10°. The direction of maximum sensitivity of the at least first sensor may particularly deviate from the surface normal of the skin contact face when the wearable electronic device is equipped with numerous sensors, e.g. arranged next to each other in or on the skin contact faces, wherein at least two of a plurality of sensors are effectively directed to a common virtual point or region of a skin portion when the wearable electronic device is suitably attached to the portion of the body of the user.

According to a further example the wearable electronic device comprises at least a second sensor connected to the processor. The second sensor is configured to acoustically detect the mechanical vibration or acoustic noise caused or generated by the click noise generator of the handheld injection device. The at least second sensor may be provided in addition to the at least first sensor. The at least second sensor may comprise a microphone. It may comprise a directional microphone.

The second sensor may be located at a predefined distance from the at least first sensor. The second sensor may be arranged and located inside the housing. It may be encapsulated inside the housing. The second sensor may be arranged in or adjacent to a sidewall of the housing of the wearable electronic device. Alternatively, the second sensor may be located on or may be embedded in a front face of the housing of the wearable electronic device. The second sensor may be arranged on a front face whereas the first sensor may be arranged in or on a bottom of the housing of the wearable sensor.

The second sensor may be configured to detect or to measure mechanical vibration or acoustic noise transmitted through air as a carrier medium. Insofar, the first sensor and the second sensor may distinguish with regard to the sensing capability in terms of a particular type of a carrier medium configured for transmission of mechanical vibration or acoustic noise.

The at least first sensor may be configured to exclusively detect mechanical vibration or acoustic noise caused or generated by the click noise generator and transmitted through biological tissue. The at least second sensor may be particularly configured to detect or to measure mechanical vibration or acoustic noise generated by the click noise generator and being transmitted through air as a carrier medium.

In this way and by having at least a first and a second sensor a mechanical vibration or acoustic noise generated or caused by the click noise generator can be recorded, monitored or detected in a redundant way. The precision of detection as well as the sensitivity of the wearable electronic device with regards to mechanical vibration or acoustic noise can be thereby increased.

With some examples, the wearable electronic device is void of the first sensor and comprises only the second sensor implemented as a microphone.

According to another example the at least first sensor is capable to detect or to measure a vibration of a skin of a user, wherein the vibration of the skin is caused or generated by the click noise generator of the handheld injection device when the handheld injection device is in mechanical contact with the user while operated by or through the user. In typical scenarios of use, the injection device is held in a hand of a user while being operated by the user. Operation of the injection device includes at least one of setting of a dose and dispensing of a dose as well as beginning or completing a dose setting or dose dispending procedure, wherein each of these actions is accompanied by the generation of a mechanical vibration or acoustic noise originating from the click noise generator.

Typically, and when the wearable electronic device is attached to the same hand or arm of the user that actually holds the handheld injection device a spatial distance between the sensor or sensors of the wearable electronic device and the click noise generator is comparatively short.

For such short distances, mechanical vibration or acoustic noise generated by the click noise generator and transferred into the biological tissue at a first position can be transmitted through the biological tissue at least to a second position, where the at least first sensor of the wearable electronic device is located.

Over comparatively short travelling distances in or across biological tissue a degree of damping or attenuation of the mechanical vibration or acoustic noise is comparatively small, so that the at least first sensor is capable to detect respective signals, e.g. at the second position. With the present example the at least first sensor is typically implemented as a vibration sensor. The vibration sensor may be implemented as an acoustic sensor, as an ultrasound sensor, as a capacitive sensor or as an optical sensor.

According to another example the at least first sensor is capable to detect or to measure a sound wave caused or generated by the click noise generator and transmitted through a portion of a body of a user when the handheld injection device is in mechanical contact with the user while being operated. Here, the at least first sensor is typically implemented as an acoustic sensor or as an ultrasound sensor. The soundwave caused or generated by the click noise generator may propagate through biological tissue, e.g. through the skin of the user or through a bone structure of the user. With some examples, a soundwave originating from the click noise generator may enter biological tissue of the user and may enter a bone structure at a first position. The soundwave may propagate through the bone structure to a second position of the bone structure located at a distance from the first position. At the second position the soundwave or a portion thereof may again propagate through biological tissue towards the at least first sensor.

A soundwave caused or generated by the click noise generator of the handheld injection device may propagate through or along at least one of a bone structure, a connective tissue, a dermal tissue or muscular tissue of a user or through combinations thereof. In general, biological tissue of the user may serve as a carrier medium for the soundwave originating from the click noise generator and detectable by the at least first sensor of the wearable electronic device when attached to a portion of a body of a user.

According to another example the wearable electronic device comprises an acceleration sensor and a gesture identifier. The gesture identifier is operable to analyze electric signals generated by the acceleration sensor. At least one of the acceleration sensor and the gesture identifier is connected to or is embedded in the processor. In this way and when attached e.g. to a hand, a wrist or an arm of a user and the user moves a respective portion of its body, the gesture identifier may identify a characteristic movement of the respective body portion. Typically, electrical signals generated by the acceleration sensor are permanently analyzed by the gesture identifier.

A characteristic gesture or movement of a portion of the body of the user leads to the generation of a characteristic sequence of electronic signals from the acceleration sensor. The gesture identifier is configured to identify such a characteristic sequence in order to determine, if for instance a person is actually grasping or lifting a pen-type or handheld injection device. Typically, the gesture identifier is capable to identify a gesture of a movement of a hand or of an arm of a user when taking the hand-held injection device for using the same.

Gesture recognition provided by the acceleration sensor and/or the gesture identifier may help to optimize electric energy consumption of the wearable electronic device. The gesture identification may also improve the precision and reliability at the detection of mechanical vibration or acoustic noise originating from the click noise generator. Moreover, with the gesture recognition a wake-up or activation routine of the wearable electronic device may be triggered.

According to a further example at least one of the gesture identifier and the processor is operable to activate the at least first sensor in response of detecting one or recognizing one of a predefined gesture, e.g. executed by the user. Detection or recognition of the predefined gesture is typically performed on the basis of electric signals generated by and obtained from the acceleration sensor when the wearable electronic device is attached to the respective portion of the body of the user.

With some examples and per default the at least first sensor may be deactivated, e.g. by the processor. If in response to a gesture recognition or gesture identification, e.g. provided by at least one of the gesture identifier or the processor, the processor may conduct a wake up routine by way of which the at least first sensor and/or the wearable electronic device is set into an activated state. In the activated state, the at least first sensor exhibits an increased level of energy consumption compared to the inactive or default state.

Per default and when switched into an activated state, the at least first sensor may remain in the activated state during a predefined time interval. When during this predefined time interval no mechanical vibration or acoustic noise should be detected by at least one of the first and second sensors the respective sensor may automatically switch into the default or inactive state. It may wake up again in response to a further gesture recognition or gesture identification.

According to another example the processor is operable to derive or to determine at least one of a size of the dose set or dispensed by the handheld injection device. Alternatively or additionally the processor is operable or capable to determine or to derive an operational status of the handheld injection device. The processor may identify e.g. an idle or an activated state of the handheld injection device. The processor may for instance determine at least one of a completion or a start of at least one of a dose setting procedure and a dose dispensing procedure. Deriving or determining of an operational status of the handheld injection device, which may also include deriving or determining of a size of a dose set or dispensed, is conducted by the processor on the basis of electric signals obtained from the at least first sensor.

Optionally or additionally, deriving or determining of the operational status and/or deriving or determining of a size of a dose may be conducted on the basis of electric signals generated by and obtained from the at least second sensor. With some examples, the processor is configured to derive and/or to determine at least one of a size of a dose or of an operational status of the handheld injection device on the basis of a combination of electric signals obtained from the first sensor and from the second sensor.

With further examples, the processor may be configured to distinguish between different operational states of the handheld injection device. For this, different operational states or different operations conducted with the handheld injection device may induce different types of mechanical vibration or different acoustic noise caused or generated by the click noise generator or caused or generated by different click noise generators.

Hence, the processor and/or at least one of the first sensor and the second sensor may be configured to distinguish between different types of mechanical vibration and/or different types of acoustic noise caused or generated, e.g. originating from different modes of operation of the click noise generator or originating from different, hence from at least a first and from at least a second click noise generator of the handheld injection device.

In order to distinguish between different types of mechanical vibration or acoustic noise electric signals provided by at least one of the first and the second sensors may be subject to an electronic filtering, such as a spectral filtering. For this, the respective sensor and/or the processor may be equipped with a suitable electronic filter operable to distinguish between first and second types of electrical signals generated by the respective sensor in response to the detection of first and second types of mechanical vibration or acoustic noise.

According to another example the wearable electronic device further comprises at least one of a memory and a communication interface. The communication interface is typically operable to exchange data with an external electronic device. The communication interface is typically implemented as a wireless communication interface. The communication interface of the wearable electronic device is typically configured to set up and to maintain a communication link with the external electronic device. The external electronic device may comprise one of a portable electronic device or stationary electronic device. With some examples the external electronic device is a smart phone, a tablet computer or a personal computer capable to establish a communication link with the wearable electronic device via the communication interface of the wearable electronic device.

The memory of the wearable electronic device as well as the communication interface are connected to the processor. In this way, electric signals obtained from at least one of the first sensor and the second sensor can either be directly stored in the memory or can be transmitted to the external electronic device. Moreover, the processor of the wearable electronic device may be operable to directly process electrical signals obtained from at least one of the first sensor and the second sensor.

The processor may be configured to directly derive or to determine at least one of a size of a dose and an operational status of the handheld injection device. The dose size and/or the operational status may either be directly transmitted to the external electronic device or may be locally stored in the memory.

With some examples, the wearable electronic device further comprises a clock by way of which data to be stored in the memory or transmitted to the external electronic device can be provided with a time or date indication. In this way, the processor and the memory may provide monitoring and/or logging of information related to the operation and/or use of the handheld injection device.

According to another example the wearable electronic device is implemented as a smart watch or as a fitness tracker. In addition to the above described features and functionality the wearable electronic device may further comprise a heartbeat sensor or pulse oximetry sensor to acquire physiologic data of a user when worn by the respective user. The wearable electronic device may provide information, such as a time and date to a user.

According to another aspect the present disclosure relates to a method of determining of at least one of a size of a dose or of an operational status of a handheld injection device. The method includes attaching a wearable electronic device to a portion of a body of a user, bringing a handheld injection device in mechanical contact with the body of the user, wherein the handheld injection device comprises a click noise generator. The method further comprises the step of detecting at least one of a mechanical vibration or an acoustic noise caused or generated by the click noise generator of the handheld injection device, when the injection device is operated by the user. The mechanical vibration or acoustic noise originating from the click noise generator may be provided during at least one of said setting of the dose, dispensing of the dose or when starting or terminating at least one of a dose dispensing or dose setting procedure.

The method further includes detecting of at least one of the mechanical vibration or acoustic noise originating from the click noise generator. Detection of the mechanical vibration or acoustic noise may include detection of the vibration or acoustic noise after having been transmitted by biological tissue, such as the skin or a bone structure of a body of a user or patient.

Furthermore, the method may further include determining or deriving at least one of a size of a dose and an operational status of the handheld injection device based on signals obtained from the at least first sensor in response to the detection of mechanical vibration or acoustic noise.

Typically, the method of determining at least one of a size of a dose or of an operational status of a handheld injection device is implemented through use of the wearable electronic device as described above. Insofar, all features, effects and benefits as described above in connection with the wearable electronic device equally apply to the method of determining the at least one of the size of the dose and the operational status of the handheld injection device; and vice versa.

According to another aspect the disclosure further relates to a computer program for determining at least one of a size of a dose set or dispensed and an operational status of a handheld injection device. Here, the handheld injection device comprises a click noise generator configured to generate a mechanical vibration or an acoustic noise during setting of a dose, during dispensing of a dose or during operation of the handheld injection device, e.g. in the course of beginning or completion at least one of a dose setting or dose dispensing procedure.

The computer program when implemented in a processor of a wearable electronic device as described above comprises computer readable instructions being operable to analyze electric signals obtained from the at least first sensor during a user-induced or user-controlled operation of the injection device, such as setting or dispensing of a dose. The computer readable instructions being further operable to determine or to derive a size of a dose currently set or dispensed by the handheld injection device and/or to determine or to derive an operational status of the handheld injection device. The deriving or determining of the operational status and/or of the dose size is provided by further computer readable instructions on the basis of the analysis of the electrical signals obtained from the at least first sensor.

Typically, the computer program is configured to be deployed in a wearable electronic device as described above. It is typically configured to be executed by the processor of the wearable electronic device. In particular, the above described method is executable with the help of the computer program. Insofar, all features, effects and benefits as described above in connection with the wearable electronic device and the method of determining at least one of a size of a dose and an operational status of the handheld injection device equally apply to the computer program; and vice versa.

Generally, the scope of the present disclosure is defined by the content of the claims. The injection device is not limited to specific embodiments or examples but comprises any combination of elements of different embodiments or examples. Insofar, the present disclosure covers any combination of claims and any technically feasible combination of the features disclosed in connection with different examples or embodiments.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin: B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza( ), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

It will be further apparent to those skilled in the art that various modifications and variations can be made to the present disclosure without departing from the scope of the disclosure. Further, it is to be noted, that any reference numerals used in the appended claims are not to be construed as limiting the scope of the disclosure.

BRIEF DESCRIPTION OF THE FIGURES

In the following, an example of the wearable electronic device usable in combination with a handheld injection device will be described in greater detail by making reference to the drawings, in which.

DETAILED DESCRIPTION

Figure 1:
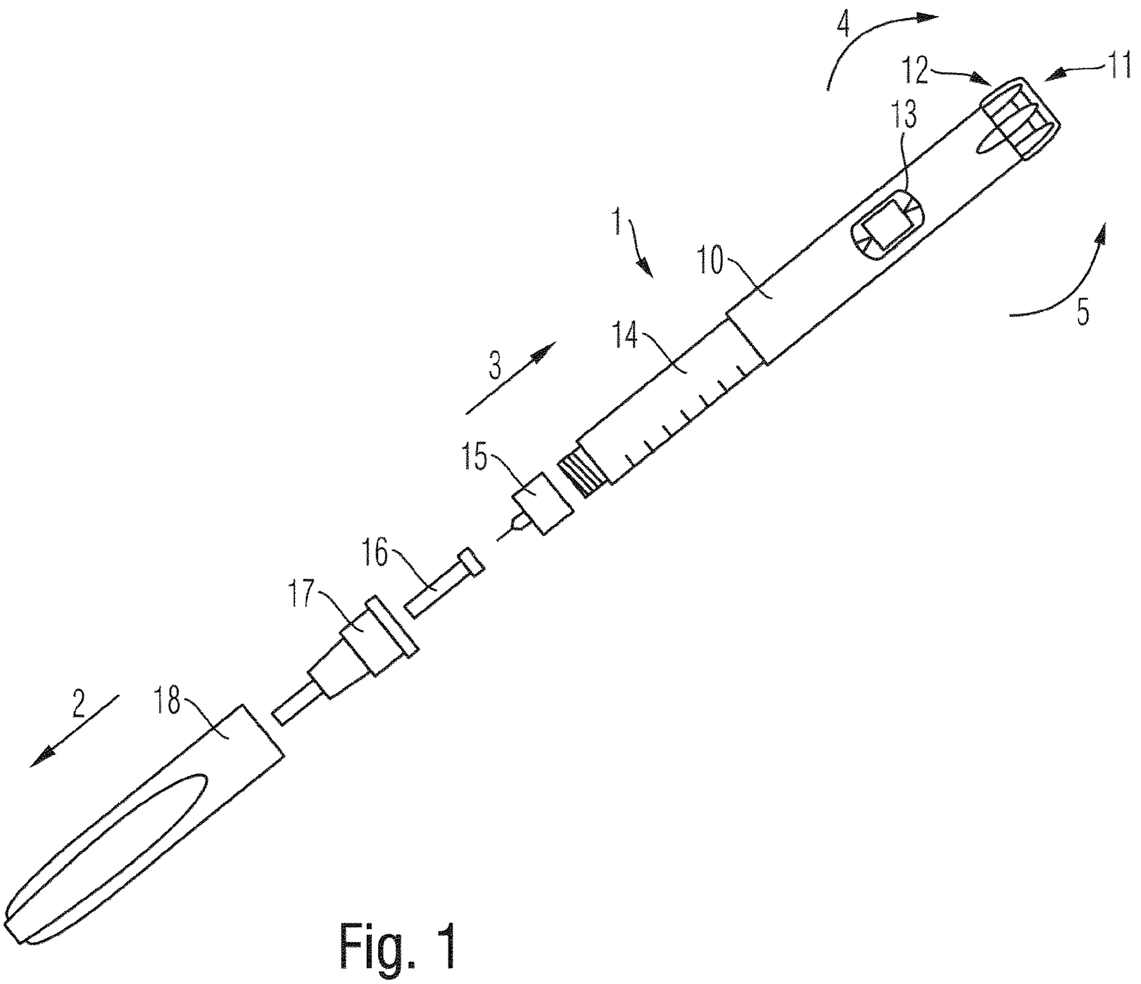
FIG. 1 schematically illustrates one example of a handheld injection device, FIG. 2 schematically shows numerous components of the handheld injection device in an exploded view.
Figure 2:
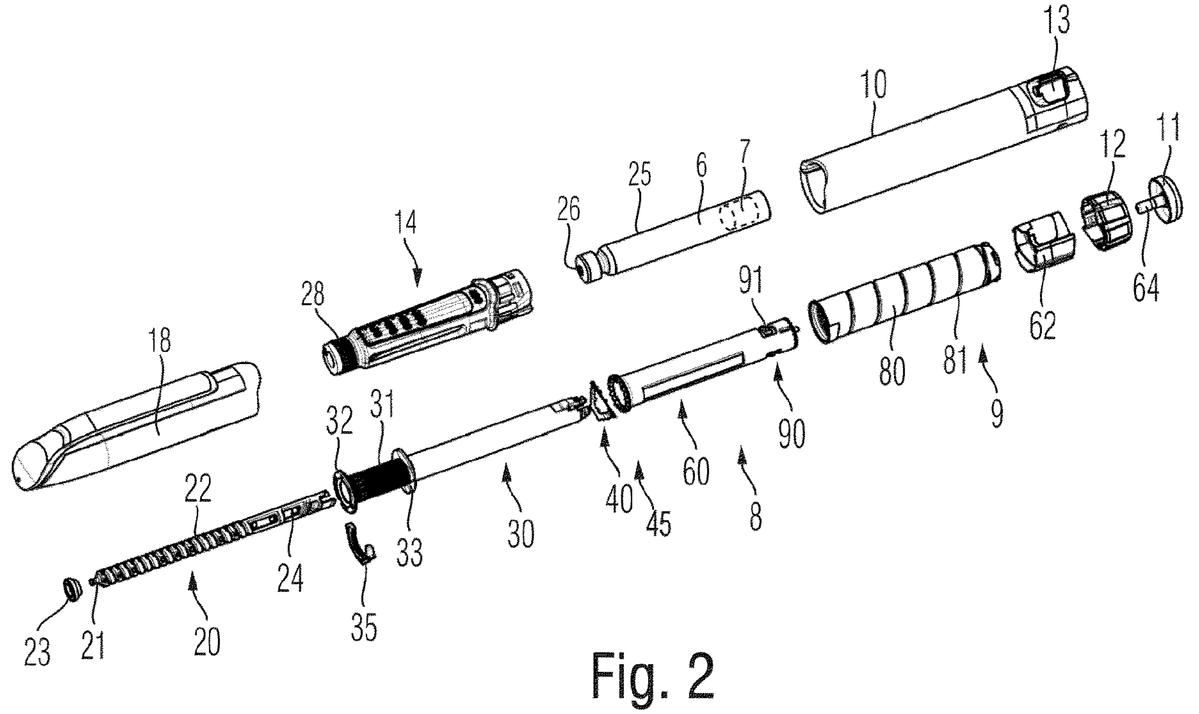

In FIGS. 1 and 2, only one of numerous examples of a handheld injection device is illustrated, that is generally usable in combination with a wearable electronic device. The device as shown in FIGS. 1 and 2 is a pre-filled disposable injection device that comprises a housing 10 to which an injection needle 15 can be affixed. The injection needle 15 is protected by an inner needle cap 16 and either an outer needle cap 17 or a protective cap 18 that is configured to enclose and to protect a distal section of the housing 10 of the injection device 1. The housing 10 may comprise and form a main housing part configured to accommodate a drive mechanism 8 and/or a dose setting mechanism 9 as shown in FIG. 2. The injection device 1 may further comprise a distal housing component denoted as cartridge holder 14. The cartridge holder 14 may be permanently or releasably connected to the main housing 10. The cartridge holder 14 is typically configured to accommodate a cartridge 6 that is filled with a liquid medicament. The cartridge 6 comprises a cylindrically-shaped or tubular-shaped barrel 25 sealed in proximal direction 3 by means of a bung 7 located inside the barrel 25. The bung 7 is displaceable relative to the barrel 25 of the cartridge 6 in a distal direction 2 by means of a piston rod 20. A distal end of the cartridge 6 is sealed by a pierceable seal 26 configured as a septum and being pierceable by a proximally directed tipped end of the injection needle 15. The cartridge holder 14 comprises a threaded socket 28 at its distal end to threadedly engage with a correspondingly threaded portion of the injection needle 15. By attaching the injection needle 15 to the distal end of the cartridge holder 14 the seal 26 of the cartridge 6 is penetrated thereby establishing a fluid transferring access to the interior of the cartridge 6.

When the injection device 1 is configured to administer e.g. human insulin, the dosage set by a dose dial 12 at a proximal end of the injection device 1 may be displayed in so-called international units (IU, wherein 1 IU is the biological equivalent of about 45.5 μg of pure crystalline insulin (1/22 mg). The dose dial 12 may comprise or may form a dose dial.

As shown further in FIGS. 1 and 2, the housing 10 comprises a dosage window 13 that may be in the form of an aperture in the housing 10. The dosage window 13 permits a user to view a limited portion of a number sleeve 80 that is configured to move when the dose dial 12 is turned, to provide a visual indication of a currently set dose. The dose dial 12 is rotated on a helical path with respect to the housing 10 when turned during setting and/or dispensing or expelling of a dose.

The injection device 1 may be configured so that turning the dosage knob 12 causes a mechanical click sound to provide acoustical feedback to a user. The click sound is typically generated by a click noise generator 45. Generally, a click noise generator 45 may be implemented in various different ways. The number sleeve 80 mechanically interacts with a piston in the insulin cartridge 6. When the needle 15 is stuck into a skin portion of a patient, and when the trigger 11 or injection button is pushed, the dose displayed in display window 13 will be ejected from injection device 1. When the needle 15 of the injection device 1 remains for a certain time in the skin portion after the trigger 11 is pushed, the dose is actually injected into the patient's body. Ejection of a dose of the liquid medicament may also cause a mechanical click sound, which is however different from the click sound produced when using the dose dial 12. For this, the injection device one may comprise a separate, hence a second click noise generator (not illustrated).

In this embodiment, during delivery of the insulin dose, the dose dial 12 is turned to its initial position in an axial movement, that is to say without rotation, while the number sleeve 80 is rotated to return to its initial position, e.g. to display a dose of zero units.

The injection device 1 may be used for several injection processes until either the cartridge 6 is empty or the expiration date of the medicament in the injection device 1 (e.g. 28 days after the first use) is reached.

An example of the drive mechanism 8 is illustrated in more detail in FIG. 2. It comprises numerous mechanically interacting components. A flange like support of the housing 10 comprises a threaded axial through opening threadedly engaged with a first thread or distal thread 22 of the piston rod 20. The distal end of the piston rod 20 comprises a bearing 21 on which a pressure foot 23 is free to rotate with the longitudinal axis of the piston rod 20 as an axis of rotation. The pressure foot 23 is configured to axially abut against a proximally facing thrust receiving face of the bung 7 of the cartridge 6. During a dispensing action the piston rod 20 rotates relative to the housing 10 thereby experiencing a distally directed advancing motion relative to the housing 10 and hence relative to the barrel 25 of the cartridge 6. As a consequence, the bung 7 of the cartridge 6 is displaced in distal direction 2 by a well-defined distance due to the threaded engagement of the piston rod 20 with the housing 10.

The piston rod 20 is further provided with a second thread 24 at its proximal end. The distal thread 22 and the proximal thread 24 are oppositely handed.

There is further provided a drive sleeve 30 having a hollow interior to receive the piston rod 20. The drive sleeve 30 comprises an inner thread threadedly engaged with the proximal thread 24 of the piston rod 20. Moreover, the drive sleeve 30 comprises an outer threaded section 31 at its distal end. The threaded section 31 is axially confined between a distal flange portion 32 and another flange portion 33 located at a predefined axial distance from the distal flange portion 32. Between the two flange portions 32, 33 there is provided a last dose limiter 35 in form of a semi-circular nut having an internal thread mating the threaded section 31 of the drive sleeve 30.

The last dose limiter 35 further comprises a radial recess or protrusion at its outer circumference to engage with a complementary-shaped recess or protrusion at an inside of the sidewall of the housing 10. In this way the last dose limiter 35 is splined to the housing 10. A rotation of the drive sleeve 30 in a dose incrementing direction 4 or clockwise direction during consecutive dose setting procedures leads to an accumulative axial displacement of the last dose limiter 35 relative to the drive sleeve 30. There is further provided an annular spring 40 that is in axial abutment with a proximally facing surface of the flange portion 33. Moreover, there is provided a tubular-shaped clutch 60. At a first end the clutch 60 is provided with a series of circumferentially directed saw teeth. Towards a second opposite end of the clutch 60 there is located a radially inwardly directed flange.

Furthermore, there is provided a dose dial sleeve also denoted as number sleeve 80. The number sleeve 80 is provided outside of the spring 40 and the clutch 60 and is located radially inward of the housing 10. A helical groove 81 is provided about an outer surface of the number sleeve 80. The housing 10 is provided with the dosage window 13 through which a part of the outer surface of the number 80 can be seen. The housing 10 is further provided with a helical rib at an inside sidewall portion of an insert piece 62, which helical rib is to be seated in the helical groove 81 of the number sleeve 80. The tubular shaped insert piece 62 is inserted into the proximal end of the housing 10. It is rotationally and axially fixed to the housing 10. There are provided first and second stops on the housing 10 to limit a dose setting procedure during which the number sleeve 80 is rotated in a helical motion relative to the housing 10.

The dose dial 12 in form of a dose dial grip is disposed about an outer surface of the proximal end of the number sleeve 80. An outer diameter of the dose dial 12 typically corresponds to and matches with the outer diameter of the housing 10. The dose dial 12 is secured to the number 80 to prevent relative movement there between. The dose dial 12 is provided with a central opening.

The trigger 11, also denoted as dose button is substantially T-shaped. It is provided at a proximal end of the injection device 10. A stem 64 of the trigger 11 extends through the opening in the dose dial 12, through an inner diameter of extensions of the drive sleeve 30 and into a receiving recess at the proximal end of the piston rod 20. The stem 64 is retained for limited axial movement in the drive sleeve 30 and against rotation with respect thereto. A head of the trigger 11 is generally circular. The trigger side wall or skirt extends from a periphery of the head and is further adapted to be seated in a proximally accessible annular recess of the dose dial 12.

To dial a dose a user rotates the dose dial 12. With the spring 40, also acting as a click noise generator 45, and the clutch 60 engaged, the drive sleeve 30, the spring 40, the clutch 60 and the number sleeve 80 rotate with the dose dial 12. Audible and tactile feedback of the dose being dialed is provided by the spring 40 and by the clutch 60. Torque is transmitted through saw teeth between the spring 40 and the clutch 60. The helical groove 81 on the number sleeve 80 and a helical groove in the drive sleeve 30 have the same lead. This allows the number sleeve 80 to extend from the housing 10 and the drive sleeve 30 to climb the piston rod 20 at the same rate. At a limit of travel a radial stop on the number sleeve 80 engages either with a first stop or a second stop provided on the housing 10 to prevent further movement in a first sense of rotation, e.g. in a dose incrementing direction 4. Rotation of the piston rod 20 is prevented due to the opposing directions of the overall and driven threads on the piston rod 20.

The last dose limiter 35 keyed to the housing 10 is advanced along the threaded section 31 by the rotation of the drive sleeve 30. When a final dose dispensed position is reached, a radial stop formed on a surface of the last dose limiter 35 abuts a radial stop on the flange portion 33 of the drive sleeve 30, preventing both, the last dose limiter 35 and the drive sleeve 30 from rotating further.

Should a user inadvertently dial beyond the desired dosage, the injection device 1, configured as a pen-injector allows the dosage to be dialed down without dispense of the medicament from the cartridge 6. For this the dose dial 12 is simply counter-rotated. This causes the system to act in reverse. A flexible arm of the spring or clicker 40 then acts as a ratchet preventing the spring 40 from rotating. The torque transmitted through the clutch 60 causes the saw teeth to ride over one another to create the clicks corresponding to dialed dose reduction. Typically, the saw teeth are so disposed that a circumferential extent of each saw tooth corresponds to a unit dose. Here, the clutch may serve as a ratchet mechanism.

As an alternative or in addition the ratchet mechanism 90 may comprise at least one ratchet feature 91, such as a flexible arm on the sidewall of the tubular-shaped clutch 60. The at least one ratchet feature 91 may comprise a radially outwardly extending protrusion e.g. on a free end of the flexible arm. The protrusion is configured to engage with a correspondingly shaped counter ratchet structure on an inside of the number sleeve 80. The inside of the number sleeve 80 may comprise longitudinally shaped grooves or protrusions featuring a saw-tooth profile. During dialing or setting of a dose the ratchet mechanism 90 allows and supports a rotation of the number sleeve 80 relative to the clutch 60 along a second sense of rotation 5, which rotation is accompanied by a regular clicking of the flexible arm of the clutch 60. An angular momentum applied to the number sleeve 80 along the first sense of rotation for is unalterably transferred to the clutch 60. Here, the mutually corresponding ratchet features of the ratchet mechanism 90 provide a torque transmission from the number sleeve 80 to the clutch 60.

When the desired dose has been dialed the user may simply dispense the set dose by depressing the trigger 11. This displaces the clutch 60 axially with respect to the number sleeve 80 causing dog teeth thereof to disengage. However, the clutch 60 remains keyed in rotation to the drive sleeve 30. The number sleeve 80 and the dose dial 12 are now free to rotate in accordance with the helical groove 81.

The axial movement deforms the flexible arm of the spring 40 to ensure the saw teeth cannot be overhauled during dispense. This prevents the drive sleeve 30 from rotating with respect to the housing 10 though it is still free to move axially with respect thereto. The deformation is subsequently used to urge the spring 40 and the clutch 60 back along the drive sleeve 30 to restore the connection between the clutch 60 and the number sleeve 80 when the distally directed dispensing pressure is removed from the trigger 11.

The longitudinal axial movement of the drive sleeve 30 causes the piston rod 20 to rotate through the through opening of the support of the housing 10, thereby to advance the bung 7 in the cartridge 6. Once the dialed dose has been dispensed, the number sleeve 80 is prevented from further rotation by contact of at least one stop extending from the dose dial 12 with at least one corresponding stop of the housing 10. A zero dose position may be determined by the abutment of one of axially extending edges or stops of the number sleeve 80 with at least one or several corresponding stops of the housing 10.

The expelling mechanism or drive mechanism 8 as described above is only exemplary for one of a plurality of differently configured drive mechanisms that are generally implementable in a disposable pen-injector. The drive mechanism as described above is explained in more detail e.g. in WO2004/078239A1, WO 2004/078240A1 or WO 2004/078241A1 the entirety of which being incorporated herein by reference.

The wearable electronic device 100 comprises a housing 101 and a wristband 102. The wristband 102 is connected to the housing 101 and provides attachment of the housing 101 and hence of the entire wearable electronic device 100 to a dedicated or selected portion 204 of the body 202 of the user. The wristband 102, typically configured as a bracelet and typically comprising a flexible strap serves to detachably fix the wearable electronic device 100 to the body portion 204 of the user such that the housing 101 gets in mechanical contact at least with the skin 200 of the user.

As illustrated in the sequence of FIGS. 5-8. the housing 101 of the wearable electronic device 100 comprises a skin contact face 103. The skin contact face 103 may be provided on a bottom 105 of the housing 101. The skin contact face 103 may coincide with the bottom 105 of the housing 101. The housing 101 further comprises a top 106 located opposite to the bottom 105. The top 106 and the bottom 105 may be integrally formed or may be interconnected by a sidewall 107 of the housing 101. Embedded in or arranged to the skin contact surface 103 there is provided at least a first sensor 160. The at least first sensor is connected to a processor 140 arranged inside the housing 101.

The at least first sensor 160 is configured to detect at least one of a mechanical vibration or an acoustic noise caused or generated by the click noise generator 45 of the handheld injection device 1. The mechanical vibration or acoustic noise is typically generated in the course of operation of the handheld injection device 1. The acoustic noise or mechanical vibration is typically transferred via the housing 10 of the handheld injection device 1 to the skin 200 and/or into the body 202 of the user. The mechanical vibration or acoustic noise may then transmit through the body 202 and/or through the skin 200 of the user towards the at least first sensor 160. The at least first sensor 160 is capable to detect at least one of the mechanical vibration or acoustic noise originating from the click noise generator 45 after being transmitted through or via the body 202.

The at least first sensor is particularly configured to exclusively detect mechanical vibration or acoustic noise that has been transmitted via the body 202 of the user. Particularly, the at least first sensor 160 is operable to detect or to quantitatively determine at least one of a mechanical vibration or an acoustic noise that has been transmitted through the skin 200. In particular, the at least first sensor may be exclusively sensitive to mechanical vibration or acoustic noise transmitted through at least one of the skin 200 or the body 202 of the user. It may be substantially insensitive to background noise provided in the surrounding or vicinity of the wearable electronic device. In this way, irrelevant background noise can be effectively suppressed or ignored. Accordingly, electrical signals generated by the first sensor 160 in response to the detection of acoustic noise or mechanical vibration transmitted via the body 202 of the user may exhibit an excellent signal-to-noise ratio.

The at least first sensor is typically implemented as one of a mechanical vibration sensor 161, an acoustic sensor 162, an ultrasound sensor 163, an electric capacity sensor 164 and an optical sensor 165. The combination and interaction between the at least first sensor 160 and the processor 140 may also provide counting of a sequence of subsequently generated mechanical vibrations or acoustic noises originating from the click noise generator 45. With typical handheld injection devices a click noise will be generated for each incremental step during setting of a dose or during dispensing of a dose. In this way and by counting the number of characteristics mechanical vibrations or acoustic noises transmitted through the body 202 and originating from the click noise generator 45 a size of a dose currently set or dispensed can be quantitatively determined.

Figure 5:
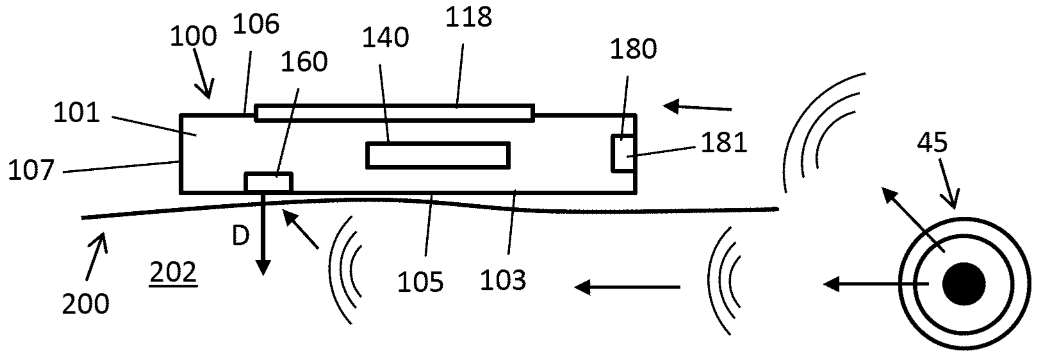

Typically, the at least first sensor 160 is directed towards a surface of the skin 200 when the wearable electronic device 100 is attached to a respective portion 204 of the body 202. As illustrated in FIG. 5, a direction D of a maximum sensitivity of the first sensor 160 is typically directed towards and/or onto the skin 200 when the wearable electronic device 100 is attached to the body portion 204. Typically, the direction D of maximum sensitivity of the at least first sensor extend substantially parallel to a surface normal of the skin contact face 103. With some examples, it may extend at an angle less than 45°, less than 30°, less than 20°, less than 15° or less than 10° with respect to the surface normal of the skin contact face 103 of the wearable electronic device 100.

Typically, the wearable electronic device 100 further comprises a display 118. The display 118 is typically provided on the top of the housing 101. The display may provide information to the user, such as time and date information as well as information about physiologic parameters of the user himself, such as a heartbeat rate and the like. When the first sensor 160 is actually detecting a mechanical vibration or an acoustic noise originating from the click noise generator 45 the processor 140 and the display 118 may be configured to provide a respective visual feedback to the user, e.g. even in real time. In this way and as the user is setting a dose with the handheld injection device respective click noises generated by the click noise generator may be recorded or detected by the at least first sensor 160.

When the processor 140 is suitably calibrated to a specific type of a handheld injection device currently in use the processor has knowledge about the dose size increment correlated to each click noise generated by the click noise generator. In this way, the processor may be operable to calculate and to visualize the size of a dose on the display 118 as soon the first sensor 160 has detected a characteristic mechanical vibration or acoustic noise originating from the handheld injection device 1.

As further illustrated in FIG. 5, the wearable electronic device 100 may be also equipped with at least a second sensor 180. The at least second sensor 180 is also connected to the processor 140. The second sensor 180 is particularly configured to acoustically detector the mechanical vibration or acoustic noise caused or generated by the click noise generator. The second sensor 180 may be implemented as a microphone 181, e.g. as a directional microphone. The second sensor 180 may further enable processing of voice commands from a user. It may be inherently provided if a conventional wearable electronic device 100 when implemented as e.g. a smart watch 110.

By having a first and a second sensor 160, 180 a mechanical vibration or an acoustic noise caused or generated by the click noise generator of the handheld injection device 1 can be recorded or monitored redundantly. In this way, the measurement precision and reliability of the detection of click noises can be substantially improved. Signals obtainable from the first sensor 160 and concurrently obtainable from the second sensor 180 may be correlated by the processor 140 in order to e.g. distinguish between mechanical vibration and acoustic noise originating from the click noise generator or originating from other sources.

As illustrated in FIG. 5, the second sensor 180 may be provided at a spatial offset from the first sensor 160. In this way, also a runtime difference of electrical signals generated by the first sensor 160 and the second sensor 180 can be used to determine, whether electrical signals of the first sensor 160 and of the second sensor 180 originating from a common source, such as the click noise generator. Here, the rather limited velocity of sound propagation or mechanical vibration propagation through biological tissue can be taken into account. A measurable runtime difference of electrical signals generated by the first sensor 160 and the second sensor 180 may be due to different lengths or different carrier media the respective sound or vibration signal is transmitted along or through.

The second sensor 118 may be located outside and offset the skin contact face 103 of the housing 101. The second sensor 180 may be located inside the housing 101. It may be located adjacent to the sidewall 107 or adjacent to the top 106.

With some examples and in particular when the wearable electronic device 100 is implemented as a smart watch 110 or as a fitness tracker the wearable electronic device 100 may comprise only one sensor operable to detect mechanical vibration or acoustic noise. Here, the first sensor 160 may comprise a microphone, e.g. a directional microphone. The first sensor 160 may be located offset from the skin contact face 103. It may e.g. coincide with the position of the second sensor 180 as illustrated in FIG. 5. Here, and particularly when implemented as a body-wearable electronic device the at least first sensor 160 comprises a microphone configured to detect mechanical vibration or acoustic noise originating from the click noise generator 45 and being predominately transmitted through air as a carrier medium.

Figure 6:
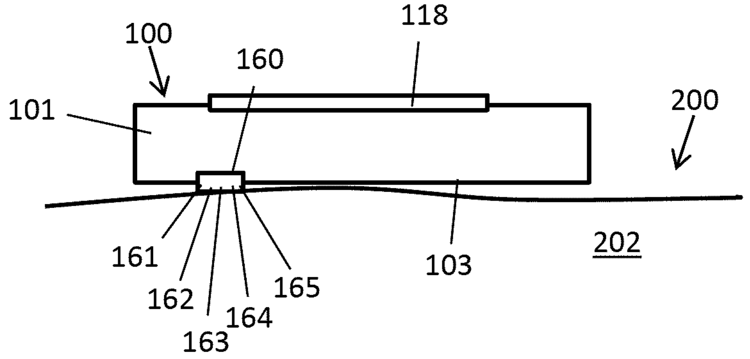

In FIG. 6, a further example of the wearable electronic device 100 is illustrated. There, the at least first sensor 160 protrudes from the skin contact face 103 at the bottom 105 of the housing 101. In this way it is somehow ensured, that the at least first sensor 160 gets in direct contact with the skin 200 when the wearable electronic device 100 is attached to a respective portion 204 of the body 202 of the user. A direct skin contact of the first sensor 160 may provide an increased precision and reliability of respective measurement results.

Figure 7:
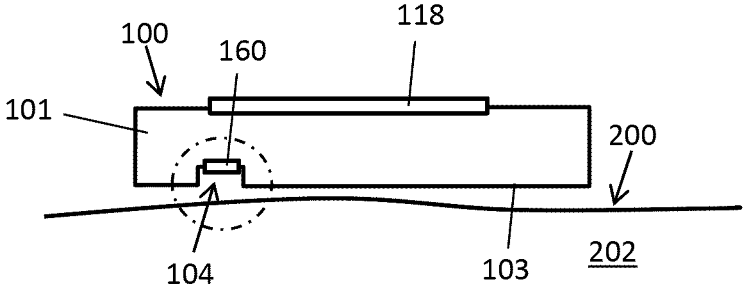
FIG. 7 shows a further example of the wearable electronic device.
Figure 8:
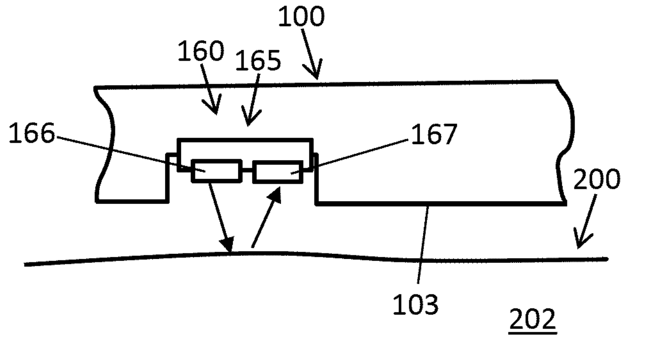
FIG. 8 shows a partial and enlarged view of the example of FIG. 7, FIG. 9 schematically illustrates one example of a click noise generator.

In the further example of FIG. 7, the at least first sensor 160 is located in a recess 104 provided in the skin contact face 103. With this example, a direct contact between the at least first sensor 160, e.g. arranged on a bottom of the recess 140 and the surface of the skin 200 can be effectively avoided. Here and as illustrated in the enlarged view of FIG. 8, the first sensor 160 may be implemented as an optical sensor 165. The optical sensor 165 may comprise a light source 166 generating light or electromagnetic radiation directed towards and onto a surface of a portion 204 of the skin 200. The optical sensor 165 further comprises an optical detector 167 by way of which at least a portion of the electromagnetic radiation generated by the light source 166 and reflected from the surface of the skin 200 can be detected. Variations in the reflected and detected light are directly indicative of e.g. vibrations of the skin 100 that may be caused by the click noise generator 45 being in direct or indirect mechanical coupling with the respective portion 204 of the body 202 of the user.

Generally, and as illustrated in FIGS. 5 and 6, the sensor 160 may be implemented as one of a vibration sensor 161 as an acoustic sensor 162, as an ultrasound sensor 163 or as a capacitive sensor 164 or as an optical sensor 165. Some of the numerous alternative implementations of the first sensor 160 are schematically indicated with only one example of the wearable electronic device 100 of FIG. 6. It is self-explanatory, that the may provide numerous wearable electronic devices, mutually distinguishing by the type and specific implementation of the first sensor 160 or the second sensor 180.

Figure 9:
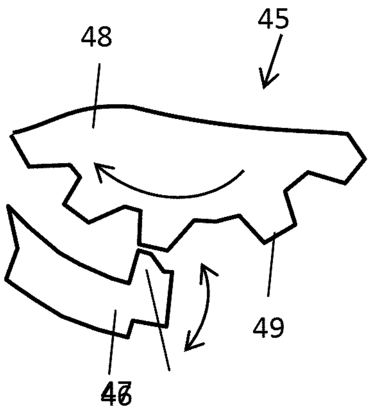

In FIG. 9, one example of a click noise generator 45 is schematically illustrated. The click noise generator 45 typically comprises a flexible or elastic part 46 provided with a protrusion 47. The protrusion 47 is configured to audibly and mechanically engage with a structure of a second component 48. The second component may comprise a toothed structure 49 that meshes with the protrusion 47 of the first component as the first component 46 and the second component 48 our subject to a movement or rotation relative to each other.

Generally, any two parts 46, 48 of a drive mechanism 8 of an injection device 1 being subject to a movement relative to each other during at least one of a dose setting or dose dispensing procedure may form or constitute a click noise generator 45.

Figure 10:
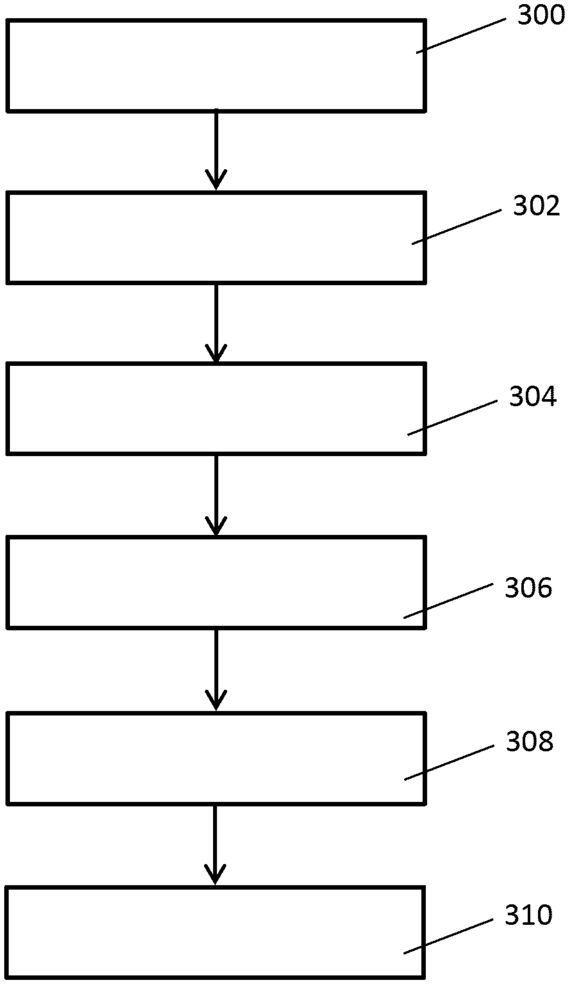
FIG. 10 shows a flowchart of the method of determining at least one of a size of a dose and an operational status of a handheld injection device.

In FIG. 10 a flowchart of the method of determining or estimating at least one of a size of a dose and an operational status of the handheld injection device 1 is illustrated. In a first step 300 the wearable electronic device 100 is attached to a portion 204 of a body 202 of a user. Typically, the wearable electronic device 100, e.g. implemented as a smart watch, is attached or fixed to a wrist of a hand 201 of the user. In a proceeding step 302 the handheld injection device is taken by the user. It is typically taken by the same hand to is also attached the wearable electronic device 100.

In a subsequent step 304, the user operates the handheld injection device 1. The user may induce or trigger at least one of a dose setting procedure, a dose dispensing procedure or some type of other routine, e.g. a check of the handheld injection device. The user-initiated operation of the handheld injection device leads to the generation of at least one of a mechanical vibration or of an acoustic noise originating from the click noise generator 45 of the handheld injection device 1. I In step 306, the respective mechanical vibration or acoustic noise is transmitted through the body 202, e.g. through the skin 200 of the user. In the subsequent step 308 the mechanical vibration or acoustic noise propagated through the body 202 is detected by the first sensor 160. In step 310, the processor 140 of the wearable electronic device 100 determines or estimates an operational status of the handheld injection device 1 and/or determines or estimates a size of a dose actually set or dispensed by the handheld injection device. Optionally, the operational status and/or the size of the dose is visually displayed on the display 118 of the wearable electronic device 100.

Figure 3:
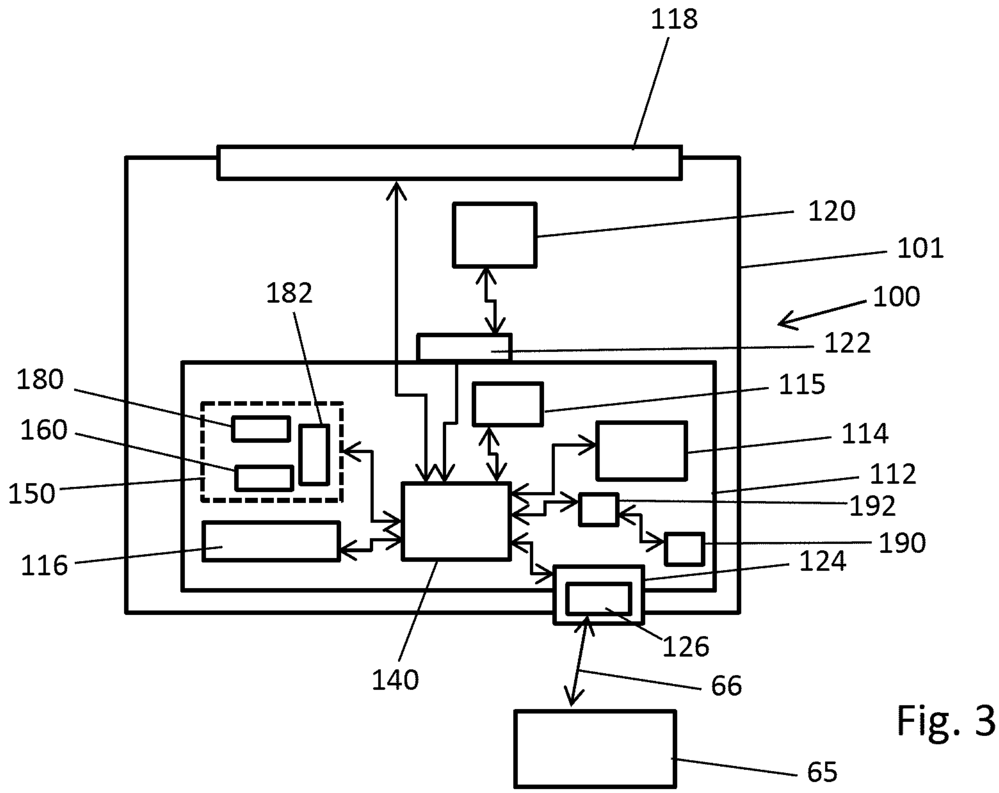
FIG. 3 shows a block diagram of logical components of the wearable electronic device.
Figure 4:
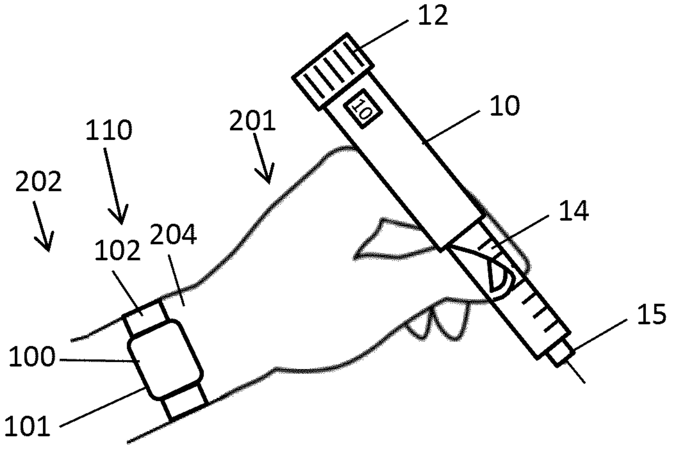
FIG. 4 is a schematic illustration of a user holding a handheld injection device in a hand and wherein a wearable electronic device is attached to a wrist of the respective hand, FIG. 5 schematically illustrates propagation of mechanical vibration and/or of acoustic noise originating from the click noise generator of the handheld injection device to be detected and/or measured by the at least first sensor of the wearable electronic device, FIG. 6 schematically illustrates a further example of the wearable electronic device.

In FIG. 3, a block diagram of the wearable electronic device 100 is schematically illustrated. The wearable electronic device 100 comprises a housing 101. The wearable electronic device 100 further comprises one or more processors 140, such as a microprocessor, a Digital Signal Processor (DSP), Application Specific Integrated Circuit (ASIC), Field Programmable Gate Array (FPGA) or the like, together with a memory 114. The memory may 114 include a program memory and main memory, which can store software for execution by the processor 140 and data generated or captured during use of the wearable electronic device 100 such as counted pulses, derived dose size, time stamp, etc. An optional switch 122 connects a power source 120 to the electronic components of the wearable electronic device 100. A display 118 may or may not be present.

The wearable electronic device 100, typically implemented as a smart watch 110 comprises an interface 124 connected to the processor 140. The interface 124 may be a wireless communications interface for communicating with another external electronic device 65, e.g. in form of a portable electronic device, via a wireless communication protocol or network such as Wi-Fi or Bluetooth®, RFID, NFC (near field communication) or BLE (Bluetooth® Low Energy). The wireless communication interface may be operable in the radio frequency range. For instance, the wireless communication interface may be based on radio-frequency identification technology (known as RFID) which allows compatible hardware to both supply power to and communicate with an otherwise unpowered and passive electronic tag using radio waves. It may be hence used for identification, authentication and tracking.

With other examples, the interface 124 is implemented as a wired communications link, such as a socket for receiving a Universal Series Bus (USB), mini-USB or micro-USB connector. For this, the interface 124 comprises a transceiver 126 configured for transmitting and receiving data. FIG. 3 depicts an example of wearable electronic device 100 connected to or connectable to an external electronic device 65 via a communication link 66 for data transfer. The data connection 66 may be of wired or wireless type.

For example, the processor 140 may store determined delivered medicament amounts and time stamps for the injections as they are administered by the user and subsequently, transfer that stored data to the external electronic device 65. The device 65 maintains a treatment log and/or forwards treatment history information to a remote location, for instance, for review by a medical professional.

The wearable electronic device 100 may act as a data collection device and may be configured to store data such as delivered medicament amounts and time stamps of numerous injection events, such as 35 or more injection events. According to a once-daily injection therapy this would be sufficient to store a treatment history of about one month. The data memory 114 may be organized in a first-in first-out manner ensuring that most recent injection events are always present in the memory of the wearable electronic device 100. Once transferred to an external electronic device 65 the injection event history in the wearable electronic device 100 might be deleted. Alternatively, the data remains in the wearable electronic device 100 and the oldest data is deleted automatically once new data is stored. This way the log in the data collection device is built up overtime during usage and will always comprise the most recent injection events. Alternatively, other configuration could comprise a storage capacity of 70 (twice daily), 100 (three months) or any other suitable number of injection events depending on the therapy requirements and/or the preferences of the user.

In another embodiment, the interface 124 may be configured to transmit information using a wireless communications link and/or the processor 140 may be configured to transmit such information to the external electronic device 65 periodically.

The processor 140 may control the optional display 118 to show the determined medicament dose information, and/or to show an elapsed time since a last medicament dose was delivered. For example, the processor 140 may cause the display 118 to switch periodically between displaying the most recent determined medicament dosage information and the elapsed time.

The power source 120 may be a battery. The power source 120 may be a coin cell, or multiple coin cells arranged in series or parallel. A timer or clock 115 may be also provided. In addition to, or instead of, switching the wearable electronic device 100 on and off, the switch 122 may be arranged to trigger the clock 115 when engaged and/or disengaged. For example, if the timer or clock 115 is triggered on both engagement or disengagement of the first and second electrical contacts of the switch or both operation and ceasing of operation of the switch 122, then the processor 140 may use the output from the timer 115 to determine a length of time during which the trigger 11 was pressed, for example to determine the duration of an injection.

Alternatively, or additionally, the processor 140 may use the timer or clock 115 to monitor a length of time that has elapsed since an injection was completed, as indicated by a time of disengagement of respective switch components or ceasing of operation of the switch 122. Optionally, the elapsed time may be shown on the display 118. Also optionally, when the switch 122 is next operated, the processor 140 may compare the elapsed time with a predetermined threshold, to determine whether a user may be attempting to administer another injection too soon after a previous injection and, if so, generate an alert such as an audible signal and/or a warning message on the display 118 or via the output 116. The output 160 may be configured to generate an audible sound or to induce a vibration hence to produce a tactile signal, e.g. for alerting the user.

The wearable electronic device may be further equipped with a sensor arrangement 150. In the illustration of FIG. 3, the sensor arrangement 150 comprises a combination of a first sensor 160 and a second sensor 180. As described above, the first sensor 160 is implemented as one of a vibration sensor 161, an acoustic sensor 162 and an ultrasound sensor 163. The first sensor 160 may also comprise a capacitive sensor 164 or an optical sensor 165. The second sensor 180 is typically implemented as a microphone 181. At least one or both of the sensors 160, 118 may be connected or coupled to an electronic filter 182. The electronic filter 182 may serve to distinguish between different characteristic signals received or generated by at least one of the first or second sensors 160, 180. The electronic filter 182, which may be also integrated into the processor 140, may help to distinguish between different types of mechanical vibration or acoustic noise detected by at least one of the first sensor 160 and the second sensor 180.

Typically, the electronic components of the wearable electronic device 100 are mutually connected by an electronic circuit 112. The electronic circuit 112 may be provided on a printed circuit board. In addition, the wearable electronic device 100 may also comprise an acceleration sensor 190 and a gesture identifier 192. The gesture identifier 192 may be also implemented or integrated into the processor 140. The acceleration sensor 190 may provide a measurement of acceleration forces present to the wearable electronic device 100. In combination with the processor 140 or in combination with the gesture identifier 192, signals obtained from the acceleration sensor 190 in response to a characteristic movement of the wearable electronic device 100 can be used to identify or to recognize a particular gesture. Such gesture recognition or identification can be further used to activate and/or to deactivate the sensor arrangement 150. If for instance the acceleration sensor 190 detects that the wearable electronic device 100 is not in a state of movement the sensor arrangement 150 may be transferred into an idle or sleep mode. When detecting a movement of the wearable electronic device 100, the processor 140 may be configured to wake up the sensor arrangement 150 or at least one of the sensor's 160, 180.

REFERENCE NUMBERS

1 injection device
2 distal direction
3 proximal direction
4 dose incrementing direction
5 dose decrementing direction
6 cartridge
7 bung
8 drive mechanism
9 dose setting mechanism
10 housing
11 trigger
12 dose dial
13 dosage window
14 cartridge holder
15 injection needle
16 inner needle cap
17 outer needle cap
18 protective cap
20 piston rod
21 bearing
22 first thread
23 pressure foot
24 second thread
25 barrel
26 seal
28 threaded socket
30 drive sleeve
31 threaded section
32 flange
33 flange
35 last dose limiter
36 shoulder
40 spring
41 recess
45 click noise generator
46 first part
47 protrusion
48 second part
49 toothed structure
60 clutch
62 insert piece
64 stem
80 number sleeve
81 groove
90 ratchet mechanism
91 ratchet feature
65 electronic device
66 data connection
100 wearable device
101 housing
102 wristband
103 skin contact face
104 recess
105 button
106 top
107 sidewall
110 smart watch
112 electronic circuit
114 memory
115 clock
116 output
118 display
120 power source
122 switch
124 interface
126 transceiver
140 processor
150 sensor arrangement
160 sensor
161 vibration sensor
162 acoustic sensor
163 ultrasound sensor
164 capacitive sensor
165 optical sensor
166 light source
167 light detector
180 sensor
181 microphone
182 electronic filter
190 acceleration sensor
192 gesture identifier
200 skin
201 hand
202 body
204 portion

The invention claimed is:

1. A wearable electronic device comprising:
a housing,
a processor arranged inside the housing, and
at least a first sensor connected to the processor and configured to detect at least one of a mechanical vibration or an acoustic noise caused or generated by a click noise generator of a handheld injection device, wherein the at least first sensor is capable to detect or to measure at least one of:
i) a vibration of a skin of a user caused or generated by the click noise generator and
ii) a sound wave caused or generated by the click noise generator (45) and transmitted through a portion of a body of a user
when the handheld injection device is in mechanical contact with the user while operated.

2. The wearable electronic device of claim 1, further comprising a wristband connected to the housing and configured to attach the housing to a portion of a body of the user.

3. The wearable electronic device of claim 1, wherein the at least first sensor is one of a mechanical vibration sensor, an acoustic sensor, an ultrasound sensor, an electric capacity sensor and an optical sensor.

4. The wearable electronic device of claim 1, wherein the housing comprises a skin contact face configured to be held in mechanical contact with a portion of a skin of the user wearing the electronic device, wherein the at least first sensor is embedded in the skin contact face or wherein the at least first sensor is arranged on the skin contact face.

5. The wearable electronic device of claim 4, wherein the at least first sensor protrudes from the skin contact face.

6. The wearable electronic device of claim 4, wherein the housing comprises a recess in the skin contact face and wherein the at least first sensor is arranged in the recess.

7. The wearable electronic device of claim 4, wherein the at least first sensor has a maximum sensitivity in a direction oriented substantially parallel to a surface normal of the skin contact face.

8. The wearable electronic device of claim 1, further comprising at least a second sensor connected to the processor and configured to acoustically detect the mechanical vibration or acoustic noise caused or generated by the click noise generator.

9. The wearable electronic device of claim 1, further comprising an acceleration sensor and a gesture identifier, the gesture identifier being operable to analyze electric signals generated by the acceleration sensor, wherein at least one of the acceleration sensor and the gesture identifier is connected to or embedded in the processor.

10. The wearable electronic device of claim 1, wherein on a basis of electric signals obtained from the at least first sensor the processor is operable to derive or to determine at least one of a size of a dose and an operational status of the handheld injection device.

11. The wearable electronic device of claim 1, wherein the wearable electronic device is implemented as a smart watch.

12. The wearable electronic device of claim 1, wherein the processor is configured to count a number of mechanical vibrations or acoustic noises of a sequence of mechanical vibrations or acoustic noises originating from the click noise generator during operation of the handheld injection device.

13. The wearable electronic device of claim 12, wherein a size of a dose set or dispensed can be calculated by counting numerous instances of repeating click noises originating from the click noise generator.

14. A method of determining of at least one of a size of a dose or of an operational status of a handheld injection device, the handheld injection device comprising a click noise generator configured to generate a mechanical vibration or an acoustic noise during operation of the handheld injection device, the method comprising:

attaching a wearable electronic device to a portion of a body of a user, wherein the wearable electronic device comprises a housing, a processor arranged inside the housing, and at least a first sensor connected to the processor and configured to detect at least one of a mechanical vibration or an acoustic noise, bringing the handheld injection device in mechanical contact with the body of the user, detecting at least one of i) a vibration of a skin of a user caused or generated by the click noise generator and ii) a sound wave caused or generated by the click noise generator (45) and transmitted through a portion of a body of a user by the at least first sensor of the wearable electronic device, and determining or deriving at least one of a size of a dose and an operational status of the handheld injection device based on signals obtained from the at least first sensor in response to the detection of mechanical vibration or acoustic noise.

15. The method of claim 14, wherein the wearable electronic device comprises a wristband connected to the housing and configured to attach the housing to the portion of the body of the user.

16. The method of claim 15, wherein the wristband may be implemented as a bracelet.

17. The method of claim 15, wherein the wristband is fixedly attached to the housing.

18. The method of claim 15, wherein the wristband provides a strap by which the wristband is wrapped around the portion of the body of the user.

19. The method of claim 14, wherein the portion of the body of the user is one of a wrist, a hand, or an arm of the user.

20. A non-transitory computer-readable medium having computer-readable instructions stored thereon for determining at least one of a size of a dose and an operational status of a handheld injection device, the handheld injection device comprising a click noise generator configured to generate a mechanical vibration or an acoustic noise during setting of a dose or during dispensing of a dose, wherein when the handheld injection device is in mechanical contact with a body of a user, and when a wearable electronic device is a attached to a body portion of the user, the computer-readable instructions, when implemented by one or more processors of the wearable electronic device, cause the one or more processors to:

detect at least one of i) a vibration of a skin of a user caused or generated by the click noise generator and ii) a sound wave caused or generated by the click noise generator (45) and transmitted through a portion of a body of a user by an at least first sensor of the wearable electronic device, analyze electrical signals obtained from the least first sensor during an operation of the handheld injection device, and determine or derive at least one of a size of a dose or of an operational status of the handheld injection device on the basis of the analysis of the electrical signals obtained from the at least first sensor, wherein the wearable electronic device comprises a housing, the one or more processors arranged inside the housing, and the at least first sensor connected to the one or more processors and configured to detect the at least one of the mechanical vibration or the acoustic noise caused or generated by the click noise generator of the handheld injection device.

* * * * *